United States Patent
Hockaday et al.

(10) Patent No.: US 11,791,023 B2
(45) Date of Patent: Oct. 17, 2023

(54) DATA COLLECTION DEVICE

(71) Applicant: MARTEL INSTRUMENTS LIMITED, Durham (GB)

(72) Inventors: Andrew Hockaday, Durham (GB); Joanne Hockaday, Durham (GB)

(73) Assignee: MARTEL INSTRUMENTS LIMITED, Durham (GB)

( * ) Notice: Subject to any disclaimer, the term of this patent is extended or adjusted under 35 U.S.C. 154(b) by 237 days.

(21) Appl. No.: 17/038,174

(22) Filed: Sep. 30, 2020

(65) Prior Publication Data
US 2021/0319857 A1    Oct. 14, 2021

(30) Foreign Application Priority Data
Apr. 8, 2020    (GB) .................................... 2005233

(51) Int. Cl.
*G16H 10/40*    (2018.01)
*G06K 7/10*    (2006.01)
*G06K 19/07*    (2006.01)

(52) U.S. Cl.
CPC ......... *G16H 10/40* (2018.01); *G06K 7/10297* (2013.01); *G06K 19/0723* (2013.01)

(58) Field of Classification Search
CPC . G16H 10/40; G06K 7/10297; G06K 19/0723
USPC .......................................................... 700/2
See application file for complete search history.

(56) References Cited

U.S. PATENT DOCUMENTS

| | | | |
|---|---|---|---|
| 5,366,896 A | 11/1994 | Margrey et al. | |
| 5,631,844 A | 5/1997 | Margrey et al. | |
| 7,732,212 B1 | 6/2010 | Nakata et al. | |
| 2005/0222778 A1 | 10/2005 | Levinson et al. | |
| 2006/0285539 A1 | 12/2006 | Eden | |
| 2011/0022323 A1 | 1/2011 | Yundt-Pacheco et al. | |
| 2013/0066563 A1 | 3/2013 | Hengstler et al. | |
| 2014/0251836 A1* | 9/2014 | Feeney | G16H 10/40 205/792 |
| 2015/0331946 A1 | 11/2015 | Balwani | |
| 2016/0020986 A1 | 1/2016 | Bosko et al. | |
| 2019/0050422 A1 | 2/2019 | Ono | |
| 2020/0105383 A1* | 4/2020 | Field | G01N 35/00732 |
| 2020/0134136 A1* | 4/2020 | Dunaway | G16B 50/00 |
| 2021/0174895 A1* | 6/2021 | Dunaway | G06F 3/0482 |
| 2021/0319857 A1* | 10/2021 | Hockaday | G06K 19/0723 |

FOREIGN PATENT DOCUMENTS

| | | |
|---|---|---|
| CN | 206058263 U | 3/2017 |
| WO | WO 2011/063139 | 5/2011 |
| WO | WO 2019/182756 | 9/2019 |

OTHER PUBLICATIONS

Search Report for corresponding Great Britain Application No. GB 2005233.8, dated Jul. 20, 2021.

* cited by examiner

*Primary Examiner* — Michael G Lee
*Assistant Examiner* — David Tardif
(74) *Attorney, Agent, or Firm* — Jason H. Vick; Sheridan Ross, PC

(57) ABSTRACT

A data collection device comprising an input, a processor and an output. The input is configured to receive a user identifier receive data from external data generating equipment. The processor is configured to generate processed data comprising the received data and metadata including the user identifier. The output is configured to output the processed data to a data repository.

19 Claims, 8 Drawing Sheets

DATA COLLECTION DEVICE

CROSS-REFERENCE TO RELATED APPLICATIONS

This application claims the benefit under 35 U.S.C. 119(a) to Great Britain Application No. 2005233.8, filed 8 Apr. 2020, the disclosure of which is incorporated herein by reference in its entirety This disclosure relates to a data collection device. In particular, but not exclusively, a data collection device may form part of a data system, and may act to interconnect data generating devices and data repositories. Certain examples of the disclosure relate particularly to a laboratory data collection device forming part of a laboratory data system interconnecting laboratory equipment and a laboratory data repository.

BACKGROUND

Data systems in which data generating devices (also known as data sources) generate data that must be processed and stored are well known. The problems of effectively and efficiently managing such a system are apparent, particularly where the data generated is large, sensitive, valuable or must be traceable. A particular example of such a data system is a laboratory. In a laboratory, particularly a commercial or teaching laboratory, there may be a range of pieces of laboratory equipment (data generating devices) capable of generating laboratory data. It is known to provide a Laboratory Information Management System (LIMS) for storing and managing data generated by laboratory equipment. A LIMS may also be referred to as an ELN (Electronic Laboratory Notebook), LIS (Laboratory Information System) or LMS (Laboratory Management System). While the definitions may vary, LIMS may be considered to be a generic term encompassing the alternative terms. For the present purposes these terms are considered to be broadly synonymous, and essentially a laboratory data repository. The term "laboratory data repository" is used herein generically to encompass particularly an LIMS or ELN. A laboratory data repository may comprise a software-based system that supports the functions of a laboratory and stores data generated by laboratory equipment.

In some laboratories it is still the case that data generated by a piece of laboratory equipment must be manually transcribed for transfer to a laboratory data repository. The risk of error is self-evident, as is the time-consuming nature of such transcription. In some known examples a laboratory data repository may be communicatively coupled to a piece of laboratory equipment so that generated data may be automatically transferred. However, presently available laboratory data repositories do not comprehensively resolve issues concerning traceability of generated data, including matching data to the underlying samples and the laboratory technicians who performed the experiments that generated the data. In addition, conventional laboratory data repositories are often proprietary and only able to be coupled to laboratory equipment from the same vendor. A large-scale laboratory may have equipment from multiple vendors: the investment in bespoke laboratory data repositories for each vendor may be prohibitive. This may drive users to less preferred ways of working, for instance manual transcription. It will be appreciated that the example of a laboratory data system is indicative of other systems where similar problems arise.

BRIEF SUMMARY OF THE DISCLOSURE

It is an aim of certain examples of the disclosure to solve, mitigate or obviate, at least partly, at least one of the problems and/or disadvantages associated with the prior art. Certain examples aim to provide at least one of the advantages described below.

According to a first aspect of the present disclosure there is provided a data collection device comprising: an input configured to: receive a user identifier; and receive data from external data generating equipment; a processor configured to generate processed data comprising the received data and metadata including the user identifier; and an output configured to output the processed data to a data repository.

Advantageously, a data collection device, for example a laboratory data collection device, according to an example of the present disclosure removes the risk of data error by removing the need for manual transactions from data generating equipment, for example laboratory equipment, to a data repository. Where manual transcription is used, typically transcribed data must be checked and authorised by a second individual. The need for this may be removed entirely through use of the disclosed laboratory collection device, and the reduction in staffing costs and test result turnaround times are self evident. Certain examples of the present disclosure provide improvements in the speed and accuracy of data collection and transfer to a data repository. A data collection device according to an example of the present disclosure may make it easier to connect equipment and data repositories from multiple vendors by being configurable to accept and output data in a format suitable for the requirements of different equipment. Furthermore, because data generated by equipment is automatically transferred to the data collection device, data security may be increased by reducing the opportunity for tampering with results. Certain examples of the present disclosure assist in meeting regulatory and compliance standards through enhancements to data security and traceability of results. Certain examples may also generate audit logs for quality control purposes in addition to session records which represent the primary data flow of the device. Operation of examples of the disclosure may save the time of technicians, and hence staff resources, and equipment costs.

According to a second aspect of the present disclosure there is provided a data system comprising: a data collection device as described above; external data generating equipment configured to generate data and to output the generated data to the data generating data collection device; and a data repository configured to receive processed data from the data collection device.

According to a third aspect of the present disclosure there is provided a method of using a data collection device comprising an input, a processor and an output, the method comprising: receiving a user identifier through the input; receiving data through the input from external data generating equipment; generating, using the processor, processed data comprising the received data and metadata including the user identifier; and outputting through the output the processed data to a data repository.

BRIEF DESCRIPTION OF THE DRAWINGS

Examples of the disclosure are further described hereinafter with reference to the accompanying drawings, in which.

DETAILED DESCRIPTION

Examples of the present disclosure presented below relate to a laboratory data collection device forming part of a laboratory data system. However, the present disclosure is not limited to laboratory use: it is applicable to any analogous system where there is a need to collect data from separate data generating equipment.

Figure 1:
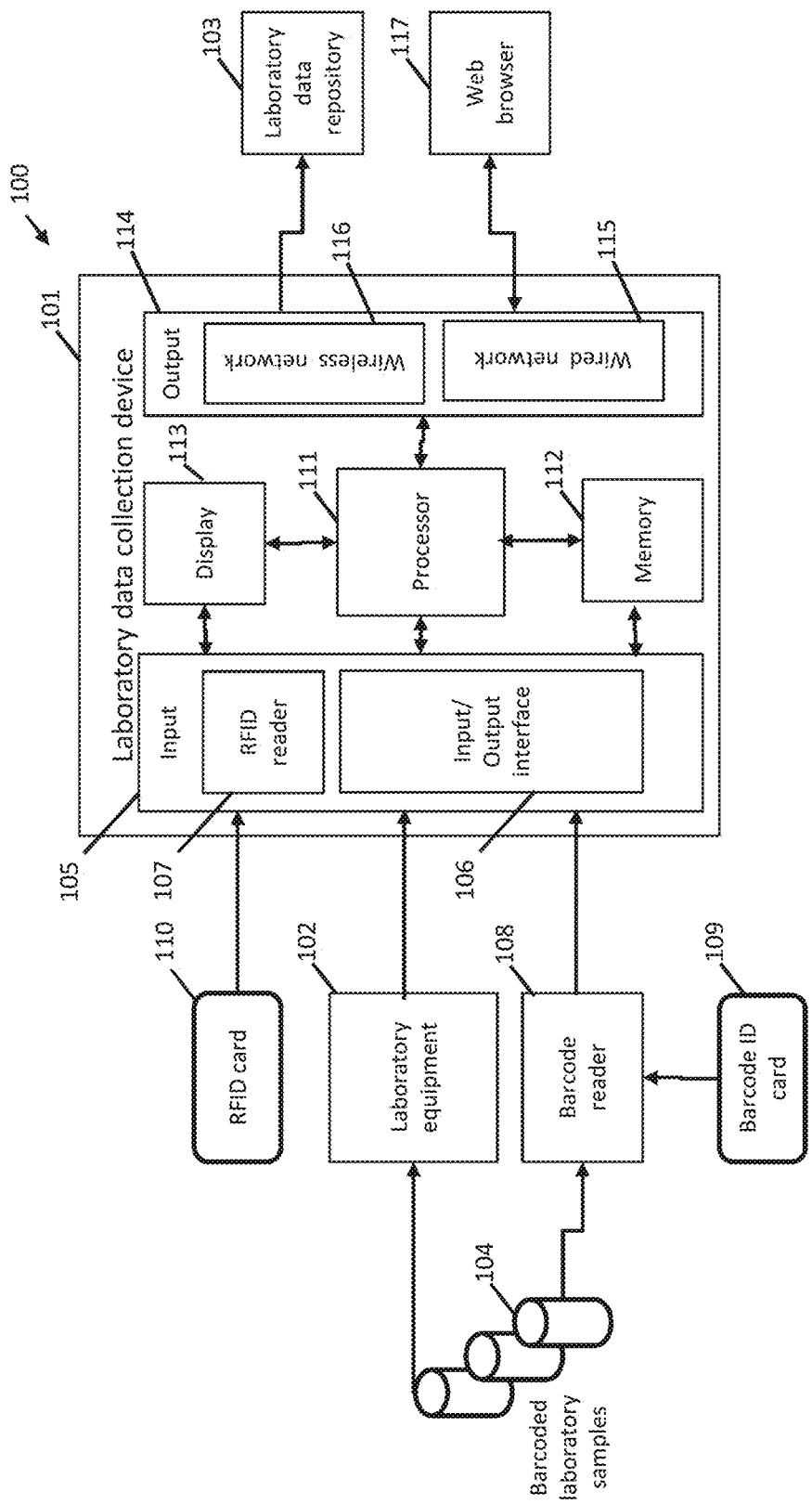
FIG. 1 schematically illustrates a laboratory data system including a laboratory data collection device according to an example of the present disclosure.

Referring now to FIG. 1, this schematically illustrates a laboratory data system 100 including a laboratory data collection device 101 according to an example of the present disclosure. The laboratory data collection device 101 interconnects at least one piece of laboratory equipment 102 to a laboratory data repository 103 in order to collect data generated by the former and transfer it to the latter for storage. The laboratory data collection device 101 may be considered to form a hub interconnecting various pre-existing parts of a laboratory data system 100. In certain examples (not illustrated) a single laboratory data collection device 101 may be coupled to more than one piece of laboratory equipment 102 and to more than one laboratory data repository 103. During operation a user may select laboratory equipment 102 to receive data from and/or select a laboratory data repository 103 to transfer data to. It may be that more than one piece of laboratory equipment 102 is selected for simultaneous receipt of data: for instance a first piece of laboratory equipment may comprise a pH meter and a second piece of laboratory equipment may comprise a thermometer such that the temperature at the time the output of the pH meter is recorded may be captured as well (either automatically when the user records the current value of the pH meter or in response to a second record operation performed by the user, as discussed below in connection with step 216 of FIG. 2).

The laboratory equipment 102 may comprise any standard or custom piece of equipment or instrument within a laboratory capable of generating a reading or other form of data which is externally accessible, for instance by being output from a data port. The generation of data may be through analysing a laboratory sample 104. The operation of the laboratory equipment 102 is outside of the scope of the present disclosure beyond it reading, generating or otherwise providing data to the laboratory data collection device 101. The laboratory data collection device 101 includes an input 105 configured to receive data from the laboratory equipment 102. In the example illustrated in FIG. 1, the input 105 includes an input/output interface 106 and an RFID (NFC) reader 107 (as will be described below). The input/output interface 106 may comprise any standard interface suitable for communicatively coupling to the laboratory equipment 102 in order to receive data from the laboratory equipment 102. For instance, the input/output interface 106 may comprise a standard RS232 serial port or USB port for a wired connection to the laboratory equipment 102. Alternatively, the laboratory data collection device 101 and the laboratory equipment 102 may communicate wirelessly. Suitable communication techniques capable of receiving data from laboratory equipment 102 will be well known to the person skilled in the art.

The laboratory data system 100 according to a first example illustrated in FIG. 1 further comprise a barcode reader 108. The barcode reader in certain examples is coupled to the input 105, and specifically the input/output interface 106, in order to provide data from a read barcode to the laboratory data collection device 101. As for the communication coupling to the laboratory equipment 102, any standard communication technique, for instance through an RS232 port, may be used. According to an example of the present disclosure, laboratory samples 104 may each be provided with a unique barcode label containing a sample ID which may be read using barcode reader 108 in order to allow the laboratory data collection device 101 to correlate data received from the laboratory equipment 102 to an ID for a particular sample 104. In alternative examples non-barcode operations may be used for identifying laboratory samples: for instance entry of a serial number using the touchscreen display 113 described below or use of the RFID reader 107 with unique RFID tags applied to laboratory samples. The operation of the barcode reader 108 and the process of generating suitable barcodes for uniquely identifying laboratory samples 104 is outside of the scope of the present disclosure, but will be well understood by the person skilled in the art. The barcode reader 108 may be used to scan the barcode for a laboratory sample 104 and to provide the read sample ID to the laboratory data collection device 101 before operation of the laboratory equipment 102 to analyse the samples 104 and generate data for transmission to the laboratory data collection device 101. It will be appreciated that in an alternative process flow the laboratory sample ID may be obtained after or substantially simultaneously with the operation of the laboratory equipment. However, with reference to FIG. 8 it will be appreciated that unless the sample ID is obtained first then the sample ID cannot be displayed along with the current data from the laboratory equipment.

The laboratory data collection device 101 is further configured to receive, through the input 105, an identifier for a user. In particular examples this may be the user who is operating the laboratory equipment 102 to analyse samples 104. Knowledge of the individual user may be used to ensure traceability, for instance for quality assurance process compliance. Additionally, knowledge of the individual user through RFID or barcode identification (or any alternative identification technique that may be substituted, such as entry of an user name and password through the display 113) may also provide for authorisation or access control: to ensure that only authorised users can use the equipment to analyse samples. The user identifier may be obtained in either of two different ways. According to a first option each user may be provided with a unique barcode ID card 109. This may be read using barcode reader 108. According to a second option each user may be provided with a unique RFID ID card 110. This may be read using the RFID reader 107 noted above to form part of input 105. The operation of an RFID reader is outside of the scope of the present disclosure but will be understood by the person skilled in the art. Similarly, processes for uniquely associating users with identifiers and issuing appropriate barcode or RFID cards will be well understood by the person skilled in the art.

The laboratory data collection device 101 further comprises a processor 111, memory 112, display 113 and output 114. The processor 111 is coupled to the input 105 and arranged to receive input data including received data generated by laboratory equipment 102 and a user identifier. The processor 111 is configured to process the received data to generate processed data including the user identifier. For example, the received data may be combined (for instance appended) with metadata including the user identifier. The metadata may further include further information, for instance time and date at which the data was received from the laboratory equipment, or the time and date at which received data was captured for storage, test reference numbers, details of raw materials and other configurable/user-specified fields. Time and date information may be obtained from an inbuilt clock (not illustrated) or alternatively may be supplied from the network using a network time protocol. Additional metadata may be obtained via input 105, for instance from laboratory equipment 102 (which may natively provide certain metadata in its output), or through the display 113 or connection to a web browser 117 as described below.

Processor 111 is coupled to memory 112. Memory 112 may store computer program instructions for operating processor 111 to perform the various processes described in this disclosure. Memory 112 may further store data generated or obtained during operation of the laboratory data collection device 101. For instance, it may store the user identifier and data received from the laboratory equipment 102 and/or processed data described above.

Display 113 may be controlled by the processor 111 in order to provide output information to the user, for instance instructions for interacting with the laboratory data collection device 101 and/or data received from the laboratory equipment 102. Display 113 may be a touch screen such as to provide an input mechanism for the user to operate the laboratory data collection device 101, as is described below in connection with the user sequence diagrams of FIGS. 2 and 11.

Output 114 is coupled to the processor 111 for outputting data from the laboratory data collection device 101. The output 114 may comprise a wired network connection 115 and/or a wireless network connection 116. Output 114 serves to output processed data under the control of processor 111 to the laboratory data repository 103. Output 114 may also allow a user to connect to the laboratory data collection device 101 through a web browser 117 on a separate computing device for configuring and controlling the laboratory data collection device 101 (as is described in more detail later in this disclosure).

Figure 2:
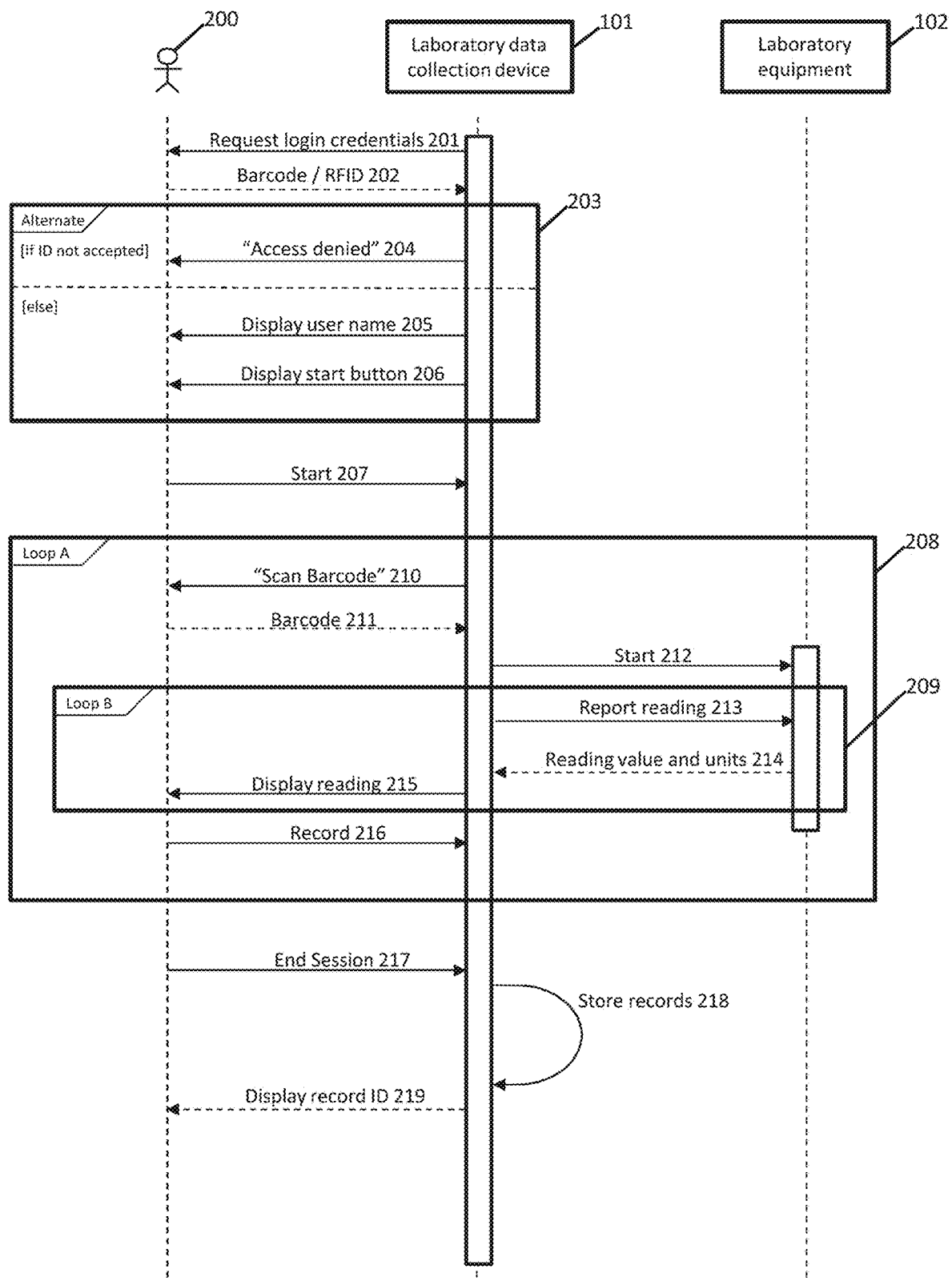
FIG. 2 illustrates a first user sequence for a user interacting with a laboratory data collection device according to an example of the present disclosure.

Referring now to FIG. 2, this illustrates a user sequence diagram showing interaction between a user 200 and a laboratory data collection device 101 according to an example of the disclosure. FIG. 2 further illustrates interaction between the laboratory data collection device 101 and laboratory equipment 102. FIG. 2 particularly highlights processes concerning obtaining a user identifier (that is, user login) and collecting data from laboratory equipment 102.

Figure 3:
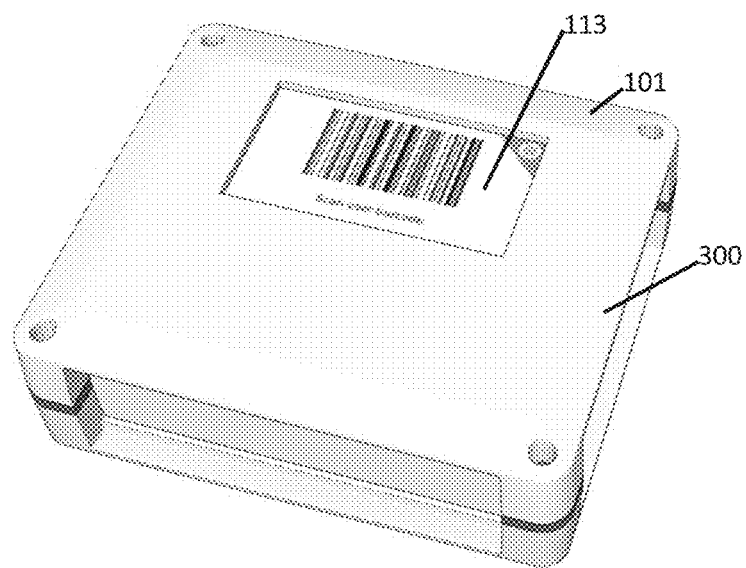
FIGS. 3 and 4 illustrate a laboratory data collection device according to an example of the present disclosure during reception of a user identifier according to first and second options.
Figure 4:
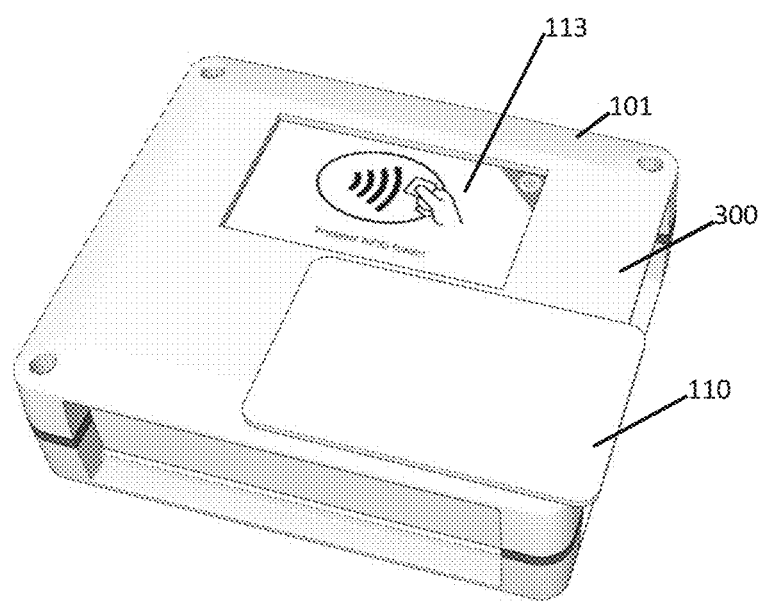

At step 201 the laboratory data collection device 101 requests the user 200 to provide login credentials. This may be a request to provide their user identifier either by use of barcode ID card 109 or an RFID ID card 110. Referring also to FIGS. 3 and 4, these figures illustrate a laboratory data collection device 101 according to an example of the disclosure, including display 113. The laboratory data collection device 101 comprises a sealed housing 300 which may be of the order of 145 mm*125 mm*50 mm (including feet, not visible in FIGS. 3 and 4). Display 113 may be exposed in an opening in housing 300 and may for instance be a 3.5" (89 mm) colour pressure-sensitive touchscreen. Any suitable display screen known to the person skilled in the art, and capable of displaying output information and receiving input touch gestures may be used. In the example of FIG. 3, the display 113 is displaying a message requesting the user to scan their user barcode ID card 109 using a barcode reader 108 coupled to the laboratory data collection device 101 (not shown in FIG. 3). In the example of FIG. 4, the display 113 is displaying a message requesting the user to present their RFID ID card 110 such that it may be read using the RFID reader 107, which is built in to the laboratory data collection device 101 within housing 300 such that it can read an RFID ID card 110 external to the housing. At step 202 the user 200 provides their user identifier. FIG. 4 illustrates RFID ID card 110 being presented to the laboratory data collection device 101.

Box 203 presents two alternatives according to whether the user identifier is accepted. The laboratory data collection device 101 may locally store a database of accepted user identifiers, including corresponding user names, within memory 112. That list may comprise a preconfigured list of users authorised to use the laboratory data collection device 101 and the connected laboratory equipment 102. Alternatively, upon receiving a user identifier through input 105, processor 111 may trigger a database lookup through the output 114. That database lookup may access an externally stored list of accepted user identifiers, for instance stored in the laboratory data repository 103 or via another connected computing device.

Figure 5:
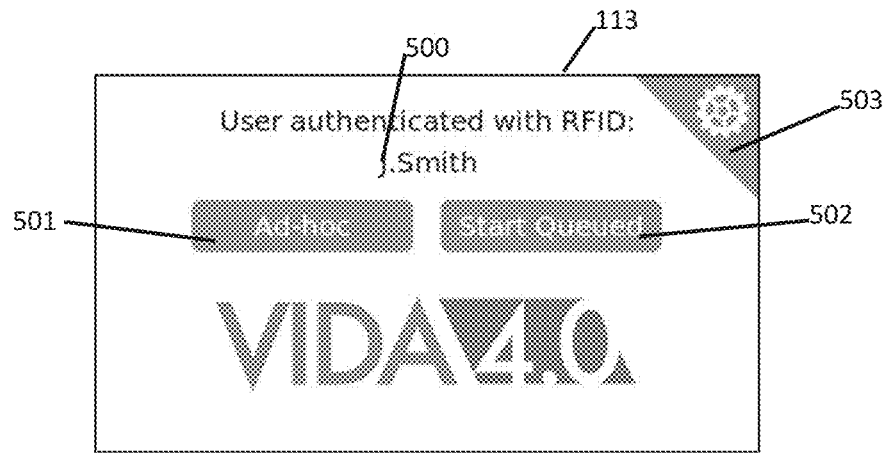
FIGS. 5 to 7 illustrate first to third options for screen displays following receipt of a user identifier for a laboratory data collection device according to an example of the present disclosure.

In the event that the received user identifier does not match one of a list of accepted user identifiers, then at step 204 the laboratory data collection device 101 returns, through display 113 a message reading "Access denied". Else, at steps 205 and 206 the corresponding user name is displayed, and a start button is displayed. Referring also to FIG. 5, this illustrates a screen displayed on display 113 in the event that a user identifier received (in this instance via the RFID reader 107) matches one of a list of accepted user identifiers. The corresponding user name ("J. Smith") 500 is displayed. Two alternative start buttons are displayed: the first start button 501 labelled "Ad-hoc" is displayed allowing a user to begin collecting data from laboratory equipment 102 without a pre-configured data collection session. The second start button 502 labelled "Start Queued" allows the user to begin collecting data from laboratory equipment 102 using a pre-configured data collection session. In an alternative there may be only a single start button, defaulting to a data collection session is one is pre-configured, else defaulting to ad-hoc. Configuration of a data collection session is described later in the present disclosure. FIG. 5 also shows a displayed icon 503 for accessing a diagnostics menu for displaying current network configuration and equipment for the laboratory data collection device 101. The settings menu will not be further described herein. FIG. 5 further shows a logo 504 for a planned commercial embodiment of the laboratory data collection device 101.

Figure 6:
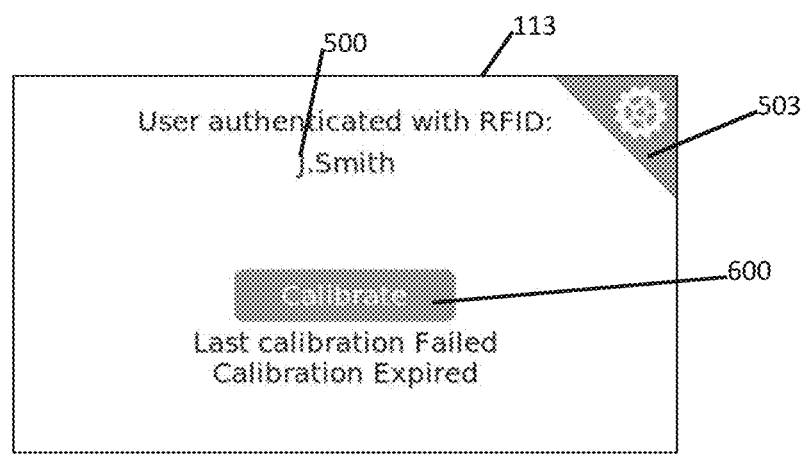
Figure 7:
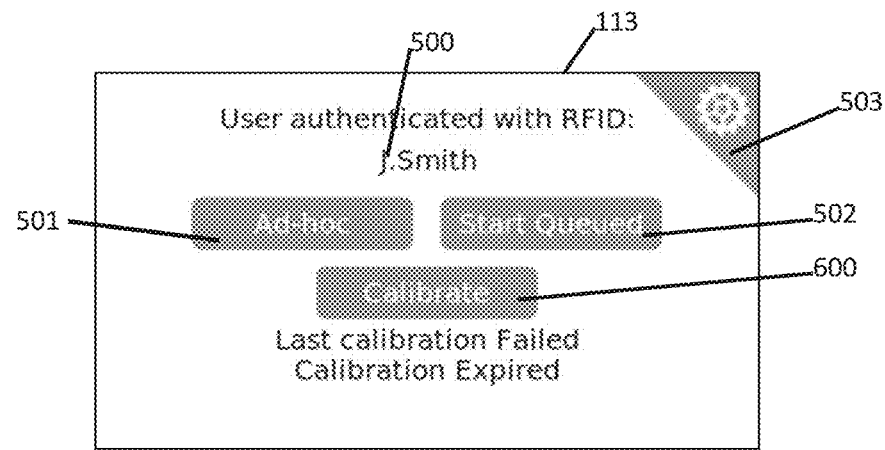

FIGS. 6 and 7 illustrate alternative screens that may be displayed on display 113 in the even that a matched user identifier is received but there is a detected need for the laboratory equipment 102 to be calibrated. Two calibration messages are displayed, though it may be that only one of the two is displayed, both indicating a need for calibration. "Last calibration failed" means that when the device was last calibrated, the result was outside of the configured acceptable tolerances. A laboratory administrator will allow laboratory equipment to continue to be used in such circumstance, so long as the "failed" note is recorded in the metadata. Alternatively, a laboratory administrator may opt instead to ensure that the equipment cannot be used if the last calibration failed. In the latter situation FIG. 6 would be displayed, while FIG. 7 would be displayed for the former situation. "Calibration Expired" means that calibration is due for the laboratory equipment, which may be detected by counting the number of measurement cycles since last calibration, as is described in greater detail later in the present disclosure. It can be seen that the corresponding user name 500 is displayed along with a calibrate button 600 for initiating a calibration sequence. FIG. 6 illustrate a first option where calibration is required, and it is not permissible to continue to use the laboratory equipment until calibration is completed. FIG. 7 differs in that while calibration is needed, the laboratory equipment 102 may continue to be used in the meantime if it is not possible or convenient to immediately perform calibration. Accordingly, in FIG. 7 the start buttons 501, 502 are also displayed. Calibration of laboratory equipment is described later in the present disclosure.

Figure 8:
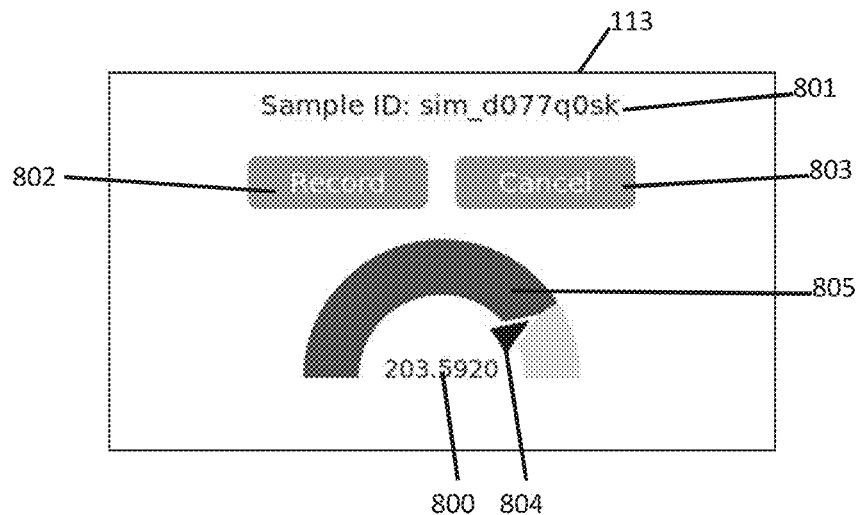
FIG. 8 illustrates a screen display during receipt of data from a piece of laboratory equipment for a laboratory data collection device according to an example of the present disclosure.
Figure 9:
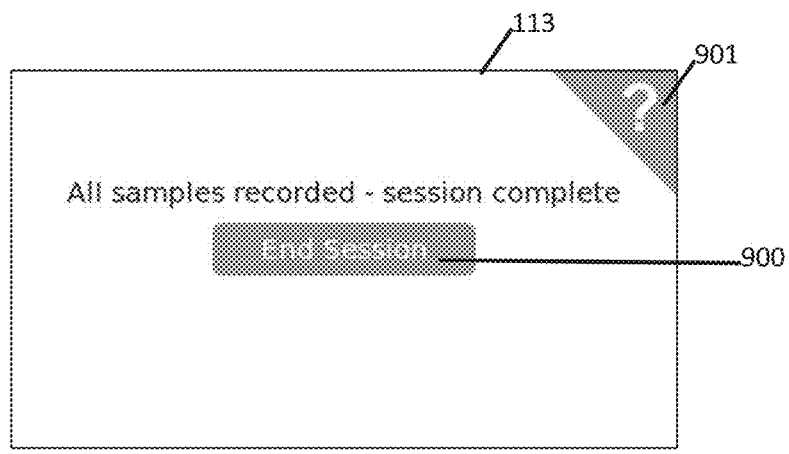
FIG. 9 illustrates a screen display at the end of a data collection session for a laboratory data collection device according to an example of the present disclosure.
Figure 10:
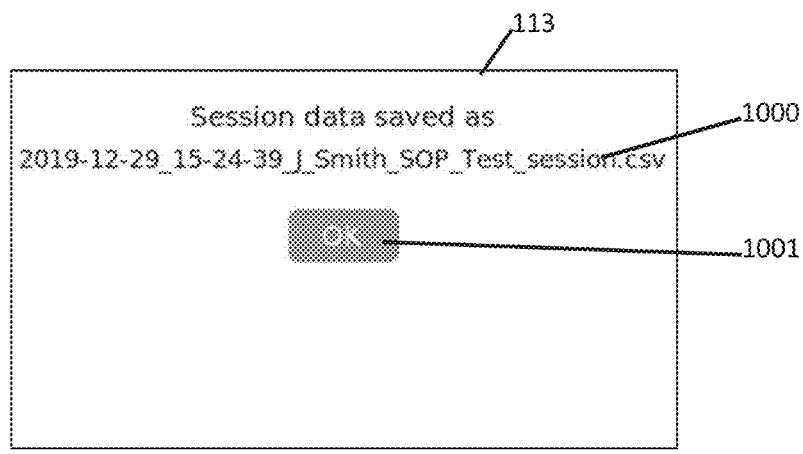
FIG. 10 illustrates a screen display following saving of session data for a laboratory data collection device according to an example of the present disclosure.

Referring back to FIG. 2, also with reference to the screen displays of FIGS. 8 to 10, if presented with a start button at step 207 the user may press a start button to begin collecting data from laboratory equipment 102. The following description applies equally to either an ad-hoc data collection operation or session or execution of a pre-configured data collection session.

FIG. 2 presents two nested loops: Loop A labelled 208 concerning the processing performed for one or more laboratory samples 104, and Loop B labelled 209 concerning the processing for a single one of the laboratory samples 104 within Loop A. Loop A begins with step 210 whereby through display 113 the user is presented with the message "Scan Barcode" (not illustrated in the screen displays of FIGS. 8 to 10). This is an instruction for the user to scan the barcode of the first sample 104 to be analysed by the laboratory equipment 102. This provides the laboratory data collection device 101 with the information to correlate data from the laboratory equipment 102 to a uniquely identified sample ID. As noted above, in other examples an alternative method may be used for identifying laboratory samples, for instance using the RFID reader or manual entry of a serial number using an displayed keypad. Steps 210 and 211, where they refer to barcodes, should be interpreted as applying equally to any suitable technique for providing the laboratory data collection device 101 with a sample ID.

Upon receipt of a barcode with a correctly formatted sample ID, the laboratory data collection device 101 may display to the user a message (not illustrated in the screen displays of FIGS. 8 to 10) indicating that the next sample 104 to be processed is, for example, "sample 1 of 3" for a pre-configured data collection session. The user may also be presented with the option to prematurely end a data collection session. The unique sample ID may also be displayed. Additionally, a check may be made whether the received sample ID is indeed unique (that is, has not be previously received for another sample.

Following receipt of an accepted sample ID the laboratory data collection device 101 may instruct the laboratory equipment 102 to begin analysis. In some examples there may be an express start instruction 212 transmitted to the laboratory equipment 102 to being operation, transmitted through the input 105. Alternatively, there may be no such transmission and the laboratory data collection device 101 may simply wait after receipt of a sample barcode for data to be received from the laboratory equipment 102.

Next, within nested loop B 209 at step 213 the laboratory data collection device 101 may transmit a message to the laboratory equipment 102 to report a reading (that is, a reading following analysis of the current sample 104). Alternatively, step 213 may be omitted and the laboratory data collection device 101 may simply wait for receipt of a reading. At step 214 the laboratory equipment 102 returns to the laboratory data collection device 101 a reading (and optionally the units of the reading). That is, the laboratory equipment 102 may return data generated through sample analysis to the laboratory data collection device 101.

At step 215 the reading is displayed to the user. This is illustrated in FIG. 8, whereby a reading 800 is displayed, along with (for this example) the sample ID 801 and buttons allowing the user to instruct the laboratory data collection device 101 to record 802 the reading or to cancel 803 the reading. FIG. 8 comprises a live representation of the reading from the laboratory equipment 102. Accordingly, loop B 209 may be repeated with the laboratory data collection device 101 optionally requesting new readings and then receiving new readings until the user selects either record 802 or cancel 803. The display 113 may also show the reading graphically, for instance through a pointer 804 upon a scale bar 805. Scale bar 805 may be preconfigured for a particular piece of laboratory equipment 102 and an anticipated range of measurement values. Optionally, the reading 800 may change colour once it is considered to have stabilised (for instance by have changed by less than a threshold amount for a preconfigured number of consecutive readings).

At step 216 within Loop A 208 the user may select the record button 802. This causes the laboratory data collection device 101 to capture the current received reading and store this along with the sample ID and metadata such as the user ID as described above. Loop A 208 then repeats allowing the user to scan a barcode for a further sample 104, either in an ad-hoc fashion for a variable number of samples 104 or for a preconfigured number of samples if a session was first established.

For a preconfigured session, with a set number of samples 104 to be analysed by laboratory equipment 102, the screen display of FIG. 9 is displayed to the user to inform them that all samples are recorded. Button 900 provides the user with the option to end the session. Alternatively, and for the case of an ad-hoc session, at step 210 where the user is requested to scan a barcode, they also be presented with the option to instead end the session. FIG. 9 also displays a question mark icon 901. Icon 901, if selected, provides a context-sensitive pop up help text according to what is currently displayed to the user. Icon 901 may be displayed additionally in any of the other screen displays described in the present disclosure.

Figure 12:
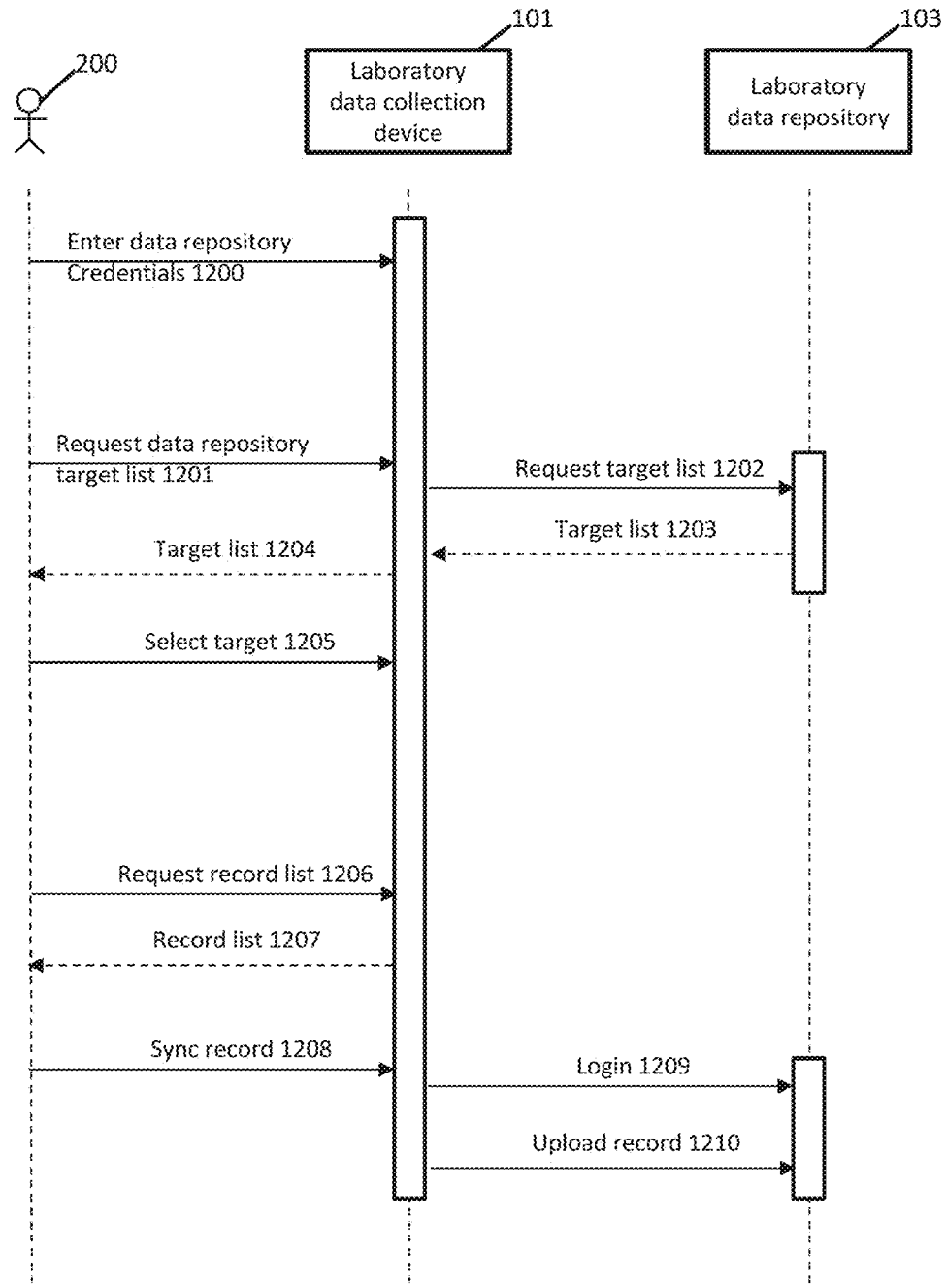
FIG. 12 illustrates a second user sequence for a user interacting with a laboratory data collection device according to an example of the present disclosure.

At step 217 the user selects the end session option and loop A 208 exits. At step 218 the laboratory data collection device 101 stores the session data for that session. For instance, the session data may comprise sample IDs and corresponding recorded readings, along with the user ID and other metadata for that session. The session data may be stored locally in memory 112. Alternatively, the session data may immediately be transmitted to laboratory data repository 103 and/or web browser 117 as well as or in place of local storage in memory 112. At step 219, and as illustrated in FIG. 10, display 113 displays a name 1000 generated for the session data. In the illustrated example this comprises a file name for a CSV (comma separated value) file storing the session data. A button labelled OK 1001 is also displayed allowing the user to close the session. It will be appreciated that the laboratory data collection device 101 is capable of storing session data in any format required by a laboratory data repository 103 and is not restricted to CSV files.

Where session data is to be output to a web browser 117 for display to the user then a human interpretable data format such as PDF (portable document file) may be used. FIG. 12 illustrates an example of session data presented as a PDF file. Column 1100 indicates the order in which samples were processed during the session. Column 1101 indicates the time and date at which the reading was recorded for each sample. Column 1102 provides the sample ID for each record in the session. Columns 1103 and 1104 provide the data generated by the laboratory equipment 102 for each sample: in this case both pH and temperature.

Figure 11:
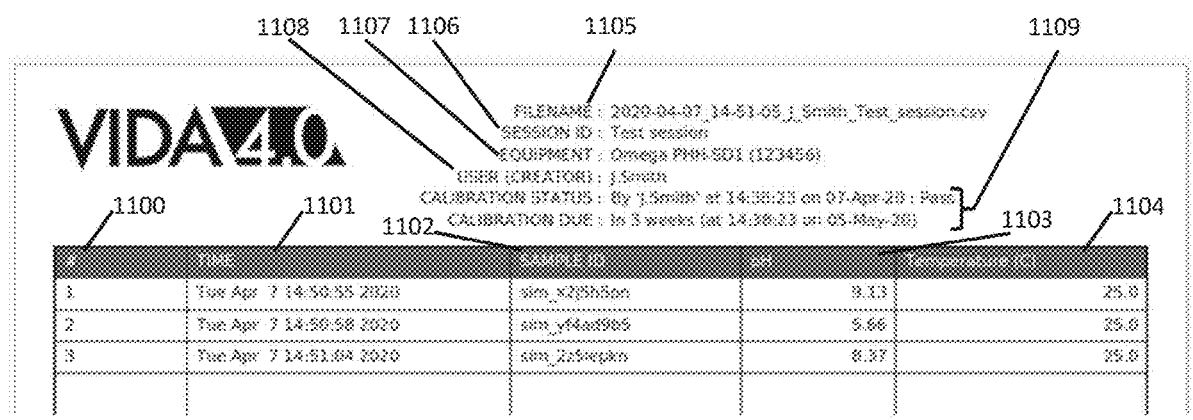
FIG. 11 illustrates an example of processed data exported by a laboratory data collection device according to an example of the present disclosure.

The session data in FIG. 11 further includes a header including filename 1105 and session ID 1106 (in the event that a named, pre-configured data collection session was started, for instance by selecting the "Start Queued" button 502 shown in FIG. 5 or 7), the particular equipment used 1107, the user 1108 whose user identifier was captured at step 202, and calibration information 1109. In the example of FIG. 11 this indicates the date and time that the laboratory equipment 102 was last calibrated, and the user who performed the calibration, and also when calibration is next due (in the example of FIG. 12, the time until the next required calibration). This information is stored in the laboratory data collection device 101 for a connected piece of laboratory equipment 101, as is described in more detail below. The equipment used 1107 may be preconfigured for the laboratory data collection device 101. If a particular laboratory data collection device 101 is configured to receive data from more than one piece of laboratory equipment 102 then data received from each piece of laboratory equipment 102 would be presented together. For instance, while FIG. 12 specifically relates to analysis of samples using a piece of laboratory equipment configured to output both pH and temperature, in another example those readings may be provided by separate pieces of equipment as described above in connection with FIG. 1. In a further option where multiple pieces of laboratory equipment 102 are connected to a single laboratory data collection device 101, the laboratory equipment 102 used for a particular data collection session may first be selected by the user.

The process of preconfiguring a data collection session will now be described. As discussed above in connection with FIG. 1, a web browser 117 upon a separate computing device may connect to the laboratory data collection device 101. The user may use the web browser to input the required data to the laboratory data collection device 101 to establish a new data collection session. Establishment of a data collection session also comprises the generation and printing of barcodes for samples 104, but this is outside of the scope of the present disclosure.

Using the web browser 117, the user may provide a quantity of samples to be analysed during the session and a session ID. This may first require the user to open an appropriate web console (not illustrated) for the laboratory data collection device 101, enter suitable user credentials (such as user name and password) and select a session set up menu option. This information may then be saved to the laboratory data collection device 101 such that upon presenting a user barcode or RFID ID card 109, 110 the start queued session button 502 is available, as illustrated in FIG. 5.

Referring now to FIG. 12, configuration of a laboratory data repository 103 will now be described. Configuration may in particular select the target location for session data to be stored within the laboratory data repository 103. It will be appreciated that this may take place prior to the processes illustrated in FIG. 1. FIG. 12 illustrates user 200 interacting directly with laboratory data collection device 101. Such interaction may be through selecting options displayed upon display 113. However, alternatively the user may interact with laboratory data collection device 101 though web browser 117. As for the establishment of a data collection session described above, this may first require the user to navigate to a web console for the laboratory data collection device 101 and enter their credentials. They may then select a suitable menu option for setting up a laboratory data repository 103.

At step 1200 the user may be prompted and then supply suitable credentials for a laboratory data repository 103 that they wish to configure. The required credentials may be specific to the particular laboratory data repository 103, but may for instance comprise a combination of username and password, API key or other repository specific authentication information. The network configuration and credentials may have been established by a system administrator in advance. The role of the system administrator is not described in detail in the present disclosure.

At step 1201, following submission and acceptance of user credentials, the user or the web browser itself may request a list of target locations within the laboratory data repository 103. This request is forwarded 1202 by the laboratory data collection device 101 to the laboratory data repository 103, which returns a list of target locations at step 1203, in turn forwarded to the user at step 1204. At step 1205 the user may select a desired location. This provides an instruction to the laboratory data collection device 101 regarding where to store future session data within the laboratory data repository 103.

Beginning at step 1206 a subsequent operation for accessing a record list of session data is described. This may not be consecutive to the process of steps 1200 to 1205. At step 1206, for instance using the web browser 117, the user 200 requests a list of records from the laboratory data collection device 101. At step 1207 the laboratory data collection device 101 returns a list of available records. This may comprise a list of session logs. Specifically, it comprises a list of available session data stored locally at the laboratory data collection device 101. The user is able to select an available session log for download to the web browser (not illustrated).

Optionally, at step 1208 the user is able to request synchronisation of session data between the laboratory data collection device 101 and the laboratory data repository 103 (particularly in the event that transfer of session data does not take place automatically upon ending a session, as described above in connection with FIGS. 9 and 10). Step 1208 comprises the user selecting a sync menu option associated with a particular session data in the session log. The current synchronisation status may be displayed. If not previously synchronised then at step 1209 the laboratory data collection device 101 may be triggered to login into the laboratory data repository 103 and upload the session data at step 1210.

A calibration process will now be described. For the purposes of the present disclosure the term "calibration" is to be interpreted as performing a test using the laboratory equipment to determine whether it is performing within defined calibration limits. The present disclosure is not concerned with any process of actually changing the performance of the connected equipment, though clearly if the test reveals that the equipment is outside of those limits the connected equipment may indeed require such a process to be performed in order to meet those limits in a follow up test. As discussed above in connection with FIGS. 6 and 7, upon acceptance of a user identifier if the connected laboratory equipment 102 is noted to require calibration then user is presented with the option to initiated calibration. In one example, calibration of a piece of laboratory equipment 102 may be considered to remain valid only for a predetermined number of measurement cycles. The laboratory data collection device 101 may keep count of the number of measurement cycles which have taken place for the or each connected piece of laboratory equipment 102. Alternatively, laboratory data collection device 101 may record the date and time at which calibration is performed and be configured with the maximum time allowed before calibration is required again. Once either the measurement cycle limit or time limit is reached the user is alerted. Whether or not they are permitted to continue to use the laboratory equipment 102 before calibration is performed may be set in advance by a system administrator. As illustrated in FIG. 11, calibration data may also be stored with session data to indicate whether the laboratory equipment 102 was correctly calibrated at the time samples were analysed. This may be simply an indication that the connected equipment is operating within defined calibration limits or, as shown in FIG. 11, more detailed information about last calibration and when this is due again. If the last calibration was failed (as described below) then this may also be indicated in session data.

In the event that calibration button 600, illustrated in FIGS. 6 and 7, is selected by the user, the laboratory data collection device 101 may provide prompts through the display to guide the user through calibration of the laboratory equipment 102. For instance, a required calibration target (that is, calibration sample) to be used may be displayed. The user may then use that calibration target to perform a measurement upon the laboratory equipment 102 as normal while the laboratory data collection device 101 displays live measurement data, as for the process of loop B 209 in FIG. 2. Laboratory data collection device 101 may be preconfigured with an acceptable measurement result (or band of results) for the calibration target. If the received measurement is acceptable then the displayed measurement reading may change colour. The user may then select a record button to record the calibration measurement. This may be stored in a calibration log accessible to a system administrator.

Figure 13:
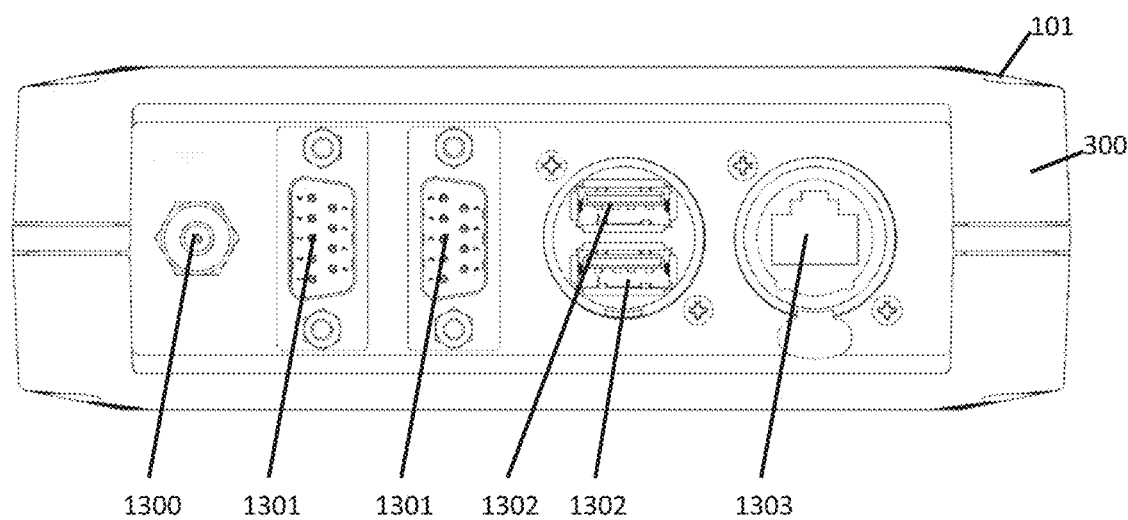
FIG. 13 illustrates the rear of a laboratory data collection device according to an example of the present disclosure.

Referring to FIG. 13, a rear panel of an example laboratory data collection device 101 will now be described. Starting from the left of FIG. 13, a power supply socket 1300 is provided. In one example, the power supply may comprise a 12 V 2 A DC power supply powered from an external AC adaptor (not illustrated). The skilled person will appreciate that the precise power supply used will depend on the power requirements of the internal components of the laboratory data collection device 101 illustrated in FIG. 1.

FIG. 13 further illustrates dual RS232 sockets 1301, dual USB sockets 1302 and an Ethernet socket 1303. The laboratory data collection device 101 may include a W-Fi network capability capable of operating in server and client mode. Additionally, alternative wireless networking protocols known to the person skilled in the art, for instance Bluetooth, may be used as well or instead of Wi-Fi. These various data input and data output options are used for connecting to laboratory equipment 102 and barcode reader 108 for receiving data and for connecting to a laboratory data repository 103. In one example, laboratory equipment 102 may be connected to an RS232 socket 1301, barcode reader 109 may be connected to a USB socket 1302 and the laboratory data repository 103 (and also a connected computing device including web browser 117) may be connected via the Ethernet 1303 or wirelessly. However, it will be appreciated that the input and output types used depend on the characteristics in particular for the connected laboratory equipment 102. For instance, laboratory equipment may be connected to a USB socket or wirelessly. Also, a wireless (particularly Bluetooth) barcode reader may be used. Furthermore, the various connection options shown in FIG. 13 may be used to connect the laboratory data collection device to additional equipment. As one example, a printer may be connected to the laboratory data collection device. This may be used to print barcodes to labelling laboratory samples. This may be configured using the web browser, and may form part of the configuration of a data collection session. A connected printer may also or alternatively be used to print out session data In one example, a single laboratory may comprise two or more laboratory data collection devices connected to multiple pieces of laboratory equipment. Furthermore, it may be that multiple such laboratory data collection devices are provided across more than one physical site. It will be appreciated that examples of the present disclosure allow those laboratory data collection devices to be configured and monitor centrally via a web console, including to establish audit logs and collect session data for quality control purposes.

A laboratory data collection device in accordance with an example of the present disclosure is configurable to operate with any piece of laboratory equipment. To function correctly requires only that the format of the data output by the equipment is understood and the laboratory data collection device be appropriately configured to accept data in that format. Similarly, it will be appreciated that the data output by a laboratory data collection device may be appropriately configured to meet the data input requirements of any existing or future laboratory data repository.

It will be appreciated that examples of the present disclosure can be realized in the form of hardware, software or a combination of hardware and software. Any such software may be stored in the form of volatile or non-volatile storage, for example a storage device like a ROM, whether erasable or rewritable or not, or in the form of memory, for example RAM, memory chips, device or integrated circuits or on an optically or magnetically readable medium, for example a CD, DVD, magnetic disk or magnetic tape or the like. It will be appreciated that the storage devices and storage media are examples of machine-readable storage that are suitable for storing a program or programs comprising instructions that, when executed, implement examples of the present disclosure.

Accordingly, examples provide a program comprising code for implementing apparatus or a method as claimed in any one of the claims of this specification and a machine-readable storage storing such a program. Still further, such programs may be conveyed electronically via any medium, for example a communication signal carried over a wired or wireless connection and examples suitably encompass the same.

Throughout the description and claims of this specification, the words "comprise" and "contain" and variations of them mean "including but not limited to", and they are not intended to (and do not) exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers or characteristics described in conjunction with a particular aspect, example or example of the disclosure are to be understood to be applicable to any other aspect, example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The disclosure is not restricted to the details of any foregoing examples. The disclosure extends to any novel one, or any novel combination, of the features disclosed in this specification (including any accompanying claims, abstract and drawings), or to any novel one, or any novel combination, of the steps of any method or process so disclosed. It will be also be appreciated that, throughout the description and claims of this specification, language in the general form of "X for Y" (where Y is some action, activity or step and X is some means for carrying out that action, activity or step) encompasses means X adapted or arranged specifically, but not exclusively, to do Y.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A data collection device comprising:
an input configured to:
receive a first user identifier; and
receive first data in a first format from a first external data generating equipment, the first external data generating equipment being a piece of laboratory equipment within a laboratory data system;
a processor configured to generate first processed data comprising the first received data and first metadata including the first user identifier, and generate first session data comprising a plurality of first processed data; and
an output configured to output the first session data to a data repository,
wherein the input is further configured to:
receive a second user identifier; and
receive second data in a second format from a second external data generating equipment, the second external data generating equipment being a second piece of laboratory equipment within the laboratory data system;
wherein the processor is further configured to generate second processed data comprising the second received data and second metadata including the second user identifier, and generate second session data comprising a plurality of second processed data;
wherein the output is further configured to output the second session data to the data repository, and
wherein the first format and the second format are different, and the first session data and the second session data have a same format.

2. The data collection device according to claim 1, further comprising a touch screen display configured to:
display data received from the first data generating equipment; and
receive a user input to record the displayed data as the first received data.

3. The data collection device according to claim 2, wherein the display is further configured to prompt the user to provide the first user identifier.

4. The data collection device according to claim 2, further configured to receive session configuration information from a user including a session identifier and a number of samples to be analysed by the first data generating equipment; and
wherein the display is further configured to display prompts for the user indicating the number of samples remaining to be analysed.

5. The data collection device according to claim 2, wherein the display is further configured to display calibration information indicating whether the first external data generating equipment requires calibration.

6. The data collection device according to claim 1, wherein the first metadata further comprises a date or time that the first data was received or recorded.

7. The data collection device according to claim 1, wherein first received data comprises an analysis result for a sample generated using the first data generating equipment;
wherein the input is further configured to receive a sample identifier for the sample; and
wherein the first metadata further comprises the sample identifier.

8. The data collection device according to claim 7, wherein the input is further configured to receive a sample identifier corresponding to a sample analysed by the first external data generating equipment to generate the first data; and
wherein the processor is further configured to include the sample identifier in the first processed data.

9. The data collection device according to claim 1, wherein first processed data corresponds to a plurality of results received from the first external data generating equipment.

10. The data collection device according to claim 1, wherein the first session data further comprises a session identifier.

11. The data collection device according to claim 1, wherein the processor is further configured to track the amount of first received data, or the time since a previous first data generating equipment calibration operation, and to provide an output indicating when the data generating equipment requires calibration.

12. The data collection device according to claim 1, further comprising a memory configured to store processed data.

13. The data collection device according to claim 1, wherein the first piece of laboratory equipment and the second piece of laboratory equipment are from different vendors.

14. The data collection device according to claim 1, wherein the first data and the second data received by the input are received simultaneously.

15. A data system comprising:
 first and second pieces of laboratory equipment configured to respectively generate data and to output the generated data to a data generating data collection device,
 the data collection device comprising:
 an input configured to:
  receive a first user identifier; and
  receive first data in a first format from the first piece of laboratory equipment within a laboratory data system;
 a processor configured to generate first processed data comprising the first received data and first metadata including the first user identifier, and generate first session data comprising a plurality of first processed data; and
 an output configured to output the first session data to a data repository;
 wherein the input is further configured to:
  receive a second user identifier; and
  receive second data in a second format from the second piece of laboratory equipment within the laboratory data system;
 wherein the processor is further configured to generate second processed data comprising the second received data and second metadata including the second user identifier, and generate second session data comprising a plurality of second processed data;
 wherein the output is further configured to output the second session data to the data repository, and
 wherein the first format and the second format are different, and the first session data and the second session data have a same format; and
 the data repository is configured to receive processed data from the data collection device.

16. The data system according to claim 15, further comprising a barcode reader coupled to the input of the data collection device;
 wherein the barcode reader is configured to read a barcode including a sample identifier applied to a sample analysed by the first piece of laboratory equipment; and
 wherein the processor is further configured to include the sample identifier in the first processed data.

17. The system according to claim 16, wherein the barcode reader is configured to scan a barcode ID card to supply the user identifier to the laboratory data collection device input; or
 wherein the data collection device input further comprises an RFID reader configured to scan an RFID card to obtain the first user identifier.

18. The system according to claim 15, further comprising a computing device including a web browser configured to connect to a web console hosted by the data collection device to provide session configuration information including a session identifier and a number of samples to be analysed by the first piece of laboratory equipment.

19. A method of using a data collection device comprising an input, a processor and an output, the method comprising:
 receiving a first user identifier through the input;
 receiving first data in a first format through the input from a first external data generating equipment in a laboratory data system;
 generating, using the processor, first processed data comprising the first received data and first metadata including the first user identifier;
 generating, using the processor, first session data comprising a plurality of first processed data; and
 outputting through the output the first processed session data to a data repository,
 wherein the method further comprises:
 receiving a second user identifier through the input;
 receiving second data in a second format through the input from a second external data generating equipment in the laboratory data system;
 generating, using the processor, second processed data comprising the second received data and second metadata including the second user identifier;
 generating, using the processor, second session data comprising a plurality of second processed data; and
 outputting through the output the second processed session data to a data repository,
 wherein the first format and the second format are different, and the first session data and the second session data have a same format.

* * * * *